US00PP20806P3

(12) United States Plant Patent

Abad Álamo et al.

(10) Patent No.: US PP20,806 P3

(45) Date of Patent: Mar. 2, 2010

(54) BLUEBERRY PLANT NAMED 'MAGNA'

(50) Latin Name: ***Vaccinium corymbosum* L.**
Varietal Denomination: Magna

(75) Inventors: Antonio Abad Álamo, Huelva (ES); José Ulf Hayler López, Huelva (ES); Paul M. Lyrene, Micanopy, FL (US)

(73) Assignee: Royal Berries S.L., Almonte (ES)

( * ) Notice: Subject to any disclaimer, the term of this patent is extended or adjusted under 35 U.S.C. 154(b) by 0 days.

(21) Appl. No.: 12/232,874

(22) Filed: Sep. 25, 2008

(65) Prior Publication Data

US 2009/0210978 P1 Aug. 20, 2009

(30) Foreign Application Priority Data

Feb. 14, 2008 (EM) ..... 20080347

(51) Int. Cl.
*A01H 5/00* (2006.01)

(52) U.S. Cl. ..... Plt./157

(58) Field of Classification Search ..... Plt./157
See application file for complete search history.

(56) References Cited

U.S. PATENT DOCUMENTS

| | | | | |
|---|---|---|---|---|
| PP10,675 | P * | 11/1998 | Lyrene | Plt./157 |
| PP12,783 | P2 * | 7/2002 | Lyrene | Plt./157 |
| PP12,816 | P2 * | 7/2002 | Lyrene | Plt./157 |
| 2009/0210983 | P1 * | 8/2009 | Abad Alamo et al. | Plt./157 |

OTHER PUBLICATIONS

UPOV ROM GTITM Computer Database, GTI Jouve Retrieval Software 2009/03 Citation for 'Magna'.*

* cited by examiner

*Primary Examiner*—Wendy C Haas
(74) *Attorney, Agent, or Firm*—Buchanan Ingersoll & Rooney PC

(57) ABSTRACT

A new and distinct Blueberry cultivar is provided that is the product of a controlled breeding program followed by selection. The cultivar flowers and forms fruit that ripens at mid-season. The attractive large light blue berries exhibit a strong acid flavor at harvest becoming sweeter a few days following harvest and which possess a very good post-harvest shelf life. The plant requires cross-pollination for abundant fruit production. The growth habit is vase-shaped and the foliage is evergreen. A low chilling requirement is also exhibited. The plant grows well in a dry climate in well-drained sandy soils.

4 Drawing Sheets

Botanical/commercial classification: *Vaccinium corymbosum* L./Blueberry Plant.

Varietal denomination: cv. Magna.

SUMMARY OF THE INVENTION

The new Blueberry cultivar of the present invention was the product of controlled artificial pollination carried out in a greenhouse at Greenwood, Fla., U.S.A., wherein two parents were crossed which previously had been studied in the hope that they would contribute the desired characteristics. The female parent (i.e., the seed parent) was the unreleased 'FL 98-19' cultivar (non-patented in the United States). The male parent (i.e., pollen parent) was the 'Millenia' cultivar (U.S. Plant Pat. No. 12,816). The parentage of the new cultivar can be summarized as follows: 'FL 98-19'×'Millenia'.

The seeds resulting from the pollination were shipped to Almonte, Huelva, Spain, where they sown during approximately 1999, small plants were obtained which were physically and biologically different from each other and selective research of the progeny was carried out. Selective study during the spring of 2003 resulted in the identification of a single plant of the new cultivar.

It was found that the new Blueberry plant of the present invention displays the following combination of characteristics:

(a) flowers and forms fruit at mid-season, (b) displays a vase-shaped growth habit with evergreen foliage, (c) Requires cross-pollination for abundant fruit production, (d) displays a low chilling requirement, and (e) forms in abundance attractive large light blue berries that commonly exhibit a strong acid flavor at harvest becoming sweeter a few days following harvest and which possess a very good post-harvest shelf life.

The new cultivar well meets the needs of the horticultural industry and can be grown to advantage for the commercial production of blueberries. The new cultivar is well adapted for growing in a dry climate in well-drained sandy soils.

The new cultivar of the present invention can be distinguished from its ancestors and all other Blueberry cultivars known to its originators. When compared to the 'Millenia' cultivar, the 'Millenia' cultivar displays more oval-shaped leaves having an acuminate to mucronate tips. When compared to the 'Sharpblue' cultivar (non-patented in the United States), the 'Sharpblue' cultivar is self-fertile and more susceptible to Aphids. When compared to the 'Windsor' cultivar (U.S. Plant Pat. No. 12,783), the 'Windsor' cultivar commonly displays a smaller more rounded growth habit. When compared to the 'Misty' cultivar (non-patented in the United States), the 'Misty' cultivar commonly forms smaller berries. When compared to the 'O'Neal' cultivar (non-patented in the United States), the 'O'Neal' cultivar commonly displays a longer chill requirement of approximately 500 hours.

The new cultivar has been asexually reproduced by the rooting of cuttings beginning during the summer of 2003 at Almonte, Huelva, Spain. Such asexual propagation has shown that the characteristics of the new cultivar are firmly fixed and are stably transmitted from one generation to another. Accordingly, the new cultivar asexually reproduces in a true to type manner.

The new cultivar has been named 'Magna'.

BRIEF DESCRIPTION OF THE PHOTOGRAPHS

The accompanying photographs show in color as nearly true as it is reasonably possible to make the same in color illustrations of this character, typical plants and plant parts of the new cultivar. The plants which had been asexually reproduced by the rooting of cuttings were approximately five years of age except where otherwise indicated, and were being grown outdoors at Almonte, Huelva, Spain.

DETAILED DESCRIPTION

Figure 1:
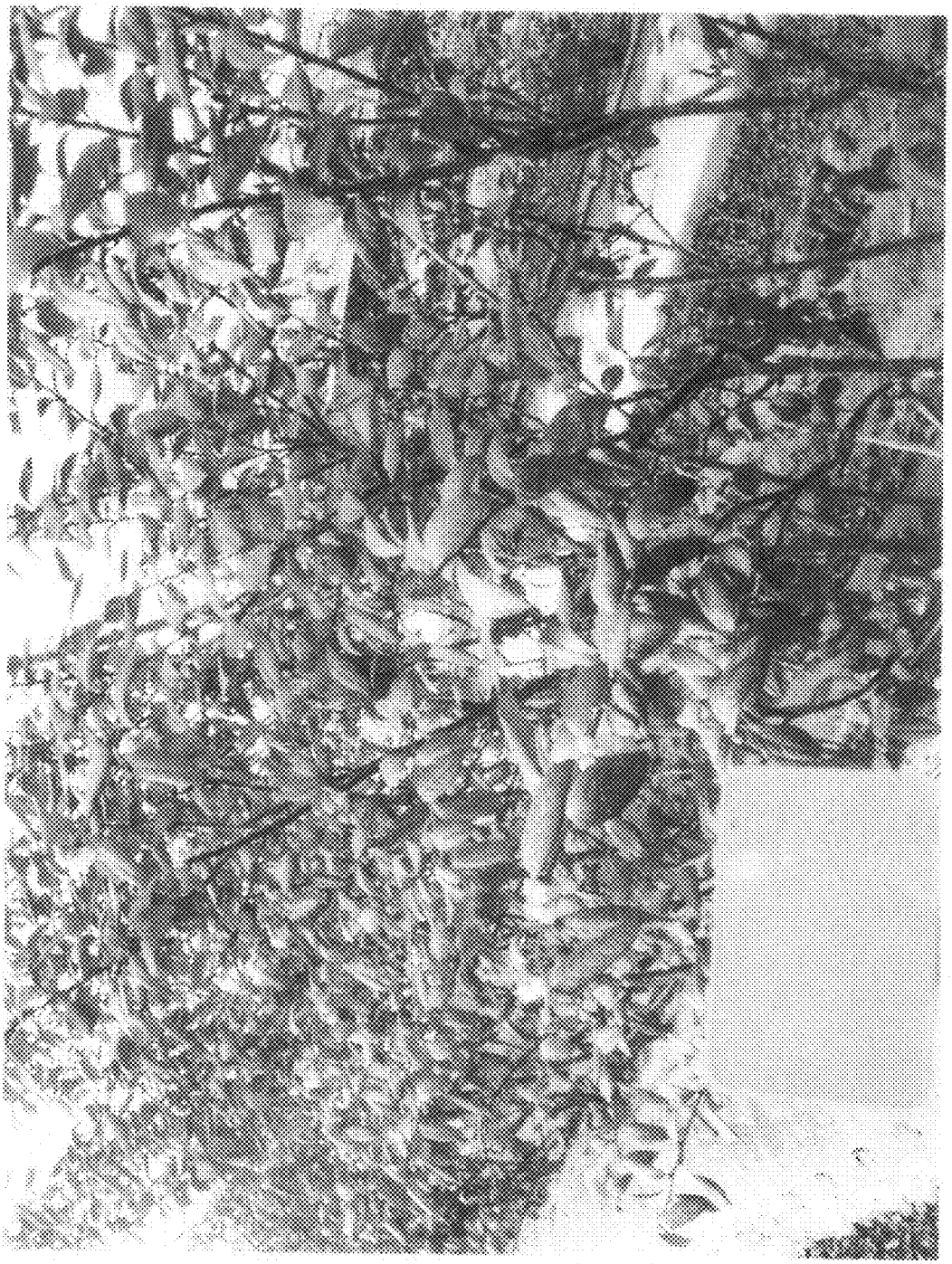
FIG. 1 shows an overall view of a row of typical plants of the new cultivar where the upright vase-shaped growth habit is apparent.
Figure 2:
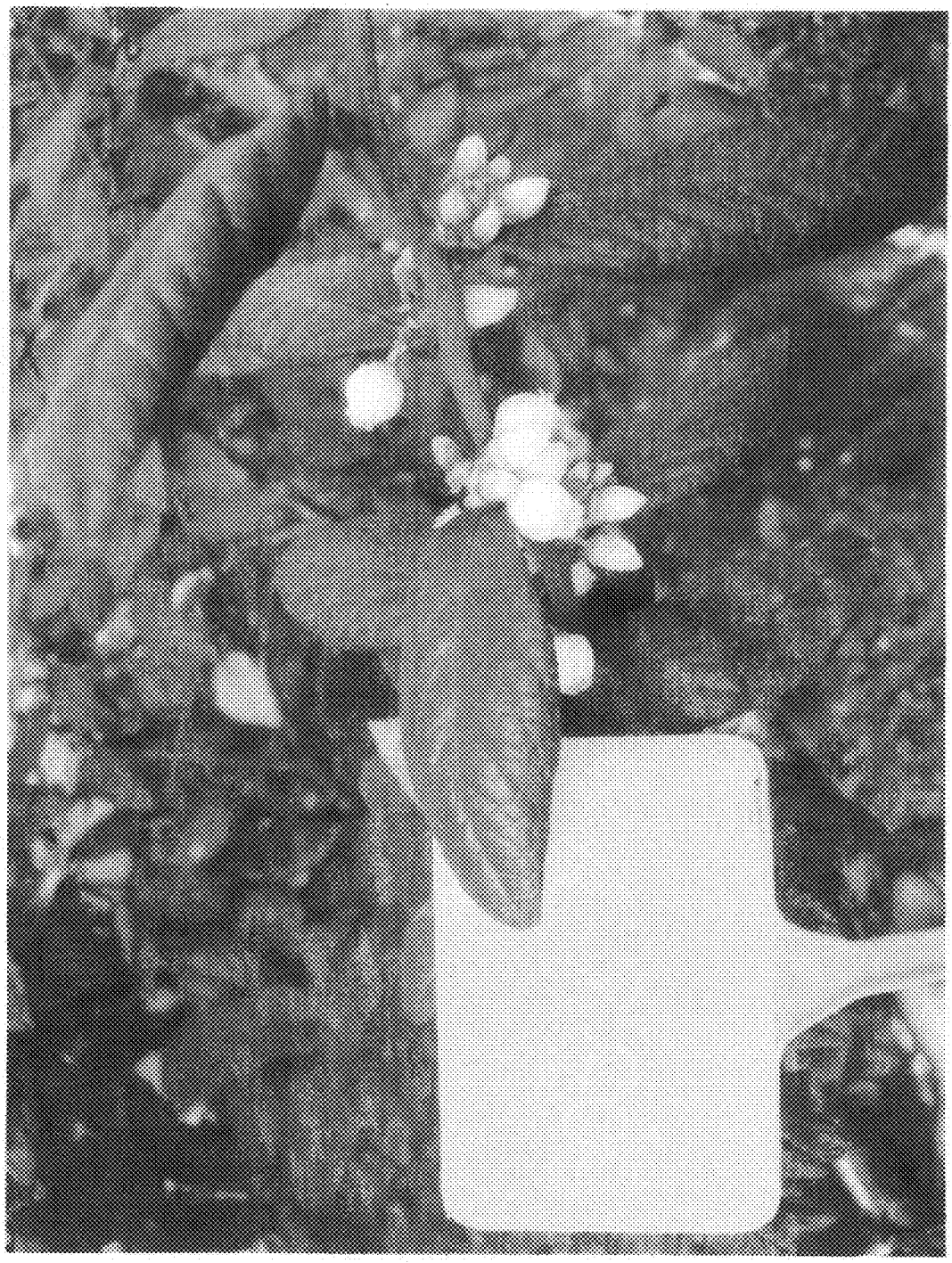
FIG. 2 shows a close view of the flowers and the upper (adaxial) surfaces of the leaves of the new cultivar.
Figure 3:
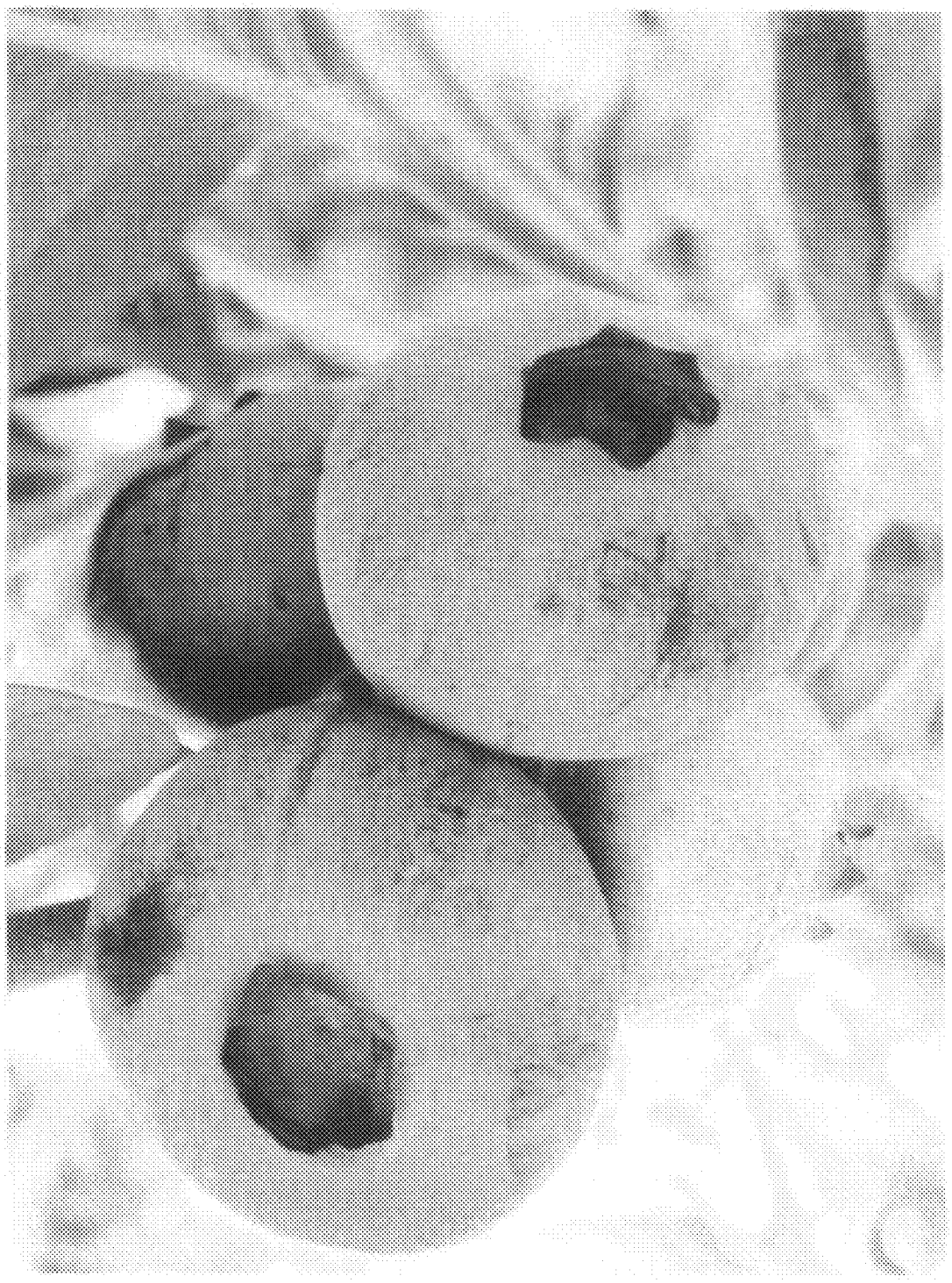
FIG. 3 shows a close view of typical berries of the new cultivar in various stages of maturity.
Figure 4:
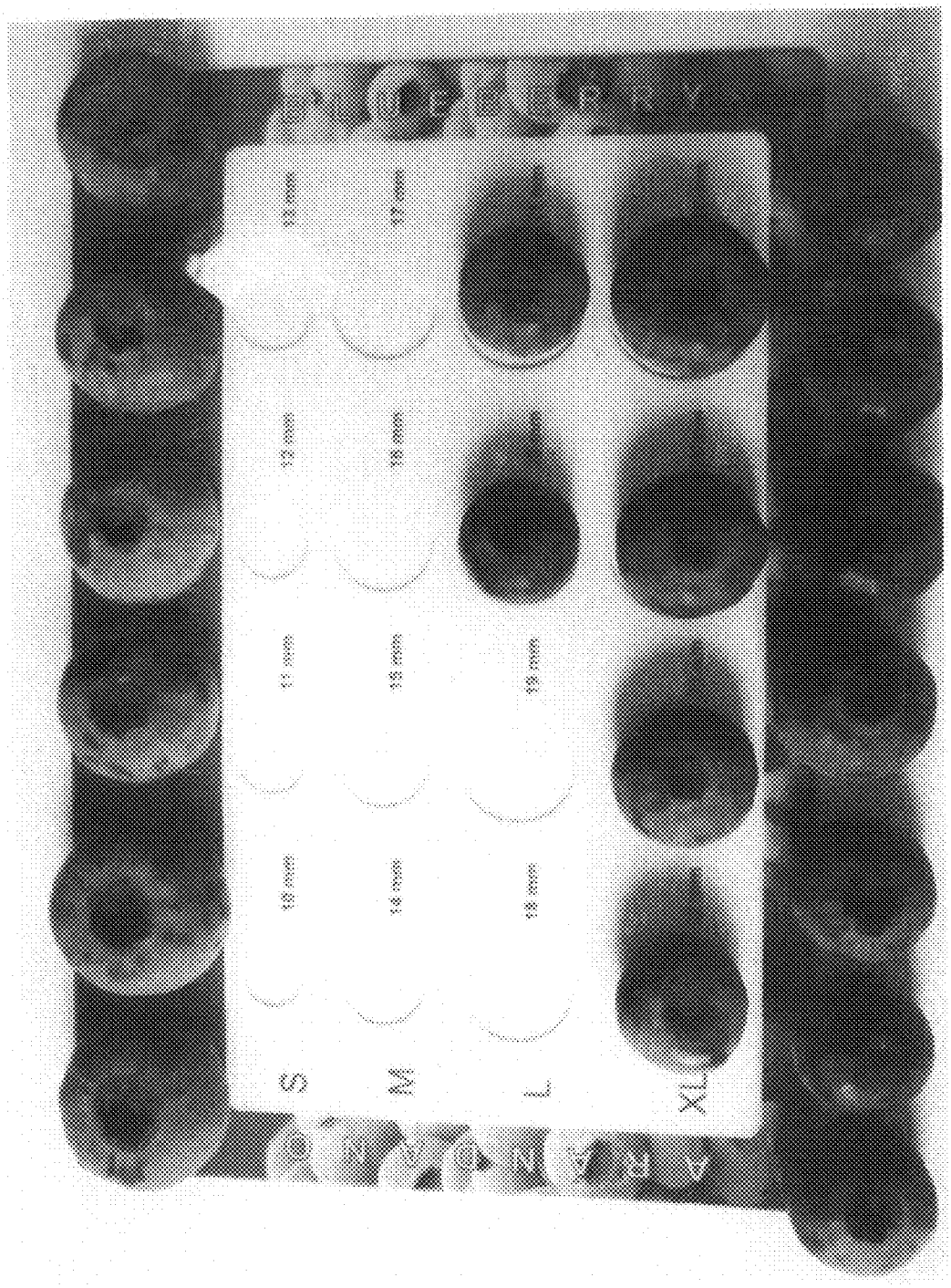
FIG. 4 shows typical mature light blue berries of the new cultivar together with a basis for size comparison.

The chart used in the identification of the colors described herein is the R.H.S. Colour Chart of the Royal Horticultural Society, London, England. Ordinary color terms are to be accorded their customary dictionary significance. The description is based on the observation of approximately five-year-old plants of the new cultivar which had been asexually reproduced by the rooting of cuttings while growing outdoors at Almonte, Huelva, Spain.

Plant:

*Growth habit.*—Vase-shaped.
*Height.*—Approximately 1.7 m at 5 years of age.
*Width.*—Approximately 3.8 m at 5 years of age.
*Foliage retention.*—Evergreen.
*Chill requirement.*—Less than 300 hours.

Foliage:

*Shape.*—Generally elliptic.
*Length.*—Commonly approximately 95 mm on average.
*Width.*—Commonly approximately 43 mm on average.
*Apex.*—Acute.
*Base.*—Acute.
*Margin.*—Entire.
*Texture.*—Glabrous and non-glandular.
*Color.*—Green Group 137C on the upper (adaxial) surface, and Green Group 138B on the under (abaxial) surface.

Flowers:

*Time.*—Medium at Almonte, Huelva, Spain, with first flower commonly at approximately November 15th, and 50 percent bloom at approximately Feb. 1st.
*Number.*—Commonly approximately 7 flowers per bud on average.
*Petals.*—5 in number and fused into a corolla tube.
*Fertility.*—Requires cross-pollination for abundant fruit production.
*Fragrance.*—Light.

Fruit:

*Time.*—Commonly from approximately Apr. 10th to Jun. 15th at Almonte, Huelva, Spain (i.e., approximately 9 weeks).
*Shape.*—Generally flattened-round and somewhat pumpkin-shaped (as illustrated).
*Height.*—Commonly approximately 15 mm on average.
*Width.*—Commonly approximately 23 mm on average.
*Weight.*—Approximately 4.26 g/berry on average during 2008 when plants were 4 years of age.
*Fruit scar.*—Approximately 2.1 mm in size.
*Fruit scar character.*—Deep and dry.
*Seed number.*—Commonly approximately 12 per berry on average.
*Seed size.*—Commonly approximately 1.1 mm in length and approximately 0.8 mm in width on average.
*Immature color.*—Commonly near Green Group 142D with bloom and Yellow-Green Group 145B without bloom.
*Mature color.*—Light blue, Violet-Blue Group 95D with bloom and Black Group 202A without bloom.
*Productivity.*—Very abundant, approximately 3.94 Kg/plant on average during 2008 when plants were 4 years of age.
*Flavor.*—Commonly displays a strong acid flavor at time of harvest becoming sweeter a few days following harvest.

Development:

*Ability to store.*—The fruit stores well under refrigeration. When stored at 20° C., approximately 91 percent of harvest commonly is of good quality 7 days after harvest, and when stored at 8° C., approximately 100 percent of the harvest commonly is of good quality 7 days after harvest.
*Disease tolerance.*—No special sensitivity to common Blueberry diseases, such as Leaf Rust (*Pucciniastrum vacinii*), Stem Blight, and Botrytis Blight (*Botrytis cinerea*), has been encountered during observations to date at Almonte, Huelva, Spain. During observations to date the new cultivar has shown to be more susceptible to Botrytis Blight than the 'Star' cultivar (U.S. Plant Pat. No. 10,675), and more susceptible to Phylophtora Root Rot than the 'Misty' cultivar.
*Insects.*—Is susceptible to aphids and thrips, and has been shown to be more resistant to Aphids than the 'Sharpblue' cultivar.
*Cultural conditions.*—Does particularly well in a dry climate in well-drained sandy soils of a low-chilling area.

Plants of the 'Magna' cultivar have not been observed under all possible environmental conditions to date, Accordingly, it is possible that the phenotypic expression may vary somewhat with changes in light intensity and duration, cultural practices, and other environmental conditions without variance in the genotype.

We claim:

1. A new and distinct Blueberry plant that possess the following combination of characteristics:

(a) flowers and forms fruit at mid-season,
(b) displays a vase-shaped growth habit with evergreen foliage,
(c) requires cross-pollination for abundant fruit production,
(d) displays a low chilling requirement, and
(e) forms in abundance attractive large light blue berries that exhibit a strong acid flavor at harvest becoming sweeter a few days following harvest and which possess a very good post-harvest shelf life;

substantially as herein shown and described.

* * * * *